United States Patent [19]

Blakemore et al.

[11] 4,394,451

[45] Jul. 19, 1983

[54] CULTURE MEDIUM AND CONDITIONS FOR GROWTH OF MAGNETIC BACTERIA

[75] Inventors: Richard P. Blakemore, Durham, N.H.; Ralph S. Wolfe, Champaign, Ill.

[73] Assignee: BioMagnetech Corp., New York, N.Y.

[21] Appl. No.: 202,160

[22] Filed: Oct. 30, 1980

[51] Int. Cl.[3] .......................... C12N 1/20; C12R 1/01; C12P 3/00
[52] U.S. Cl. .................................. 435/253; 435/822; 435/168
[58] Field of Search ............... 435/253, 168, 170, 822, 435/243

[56] References Cited

PUBLICATIONS

Blakemore, R., "Magnetotatic Bacteria", *Science;* vol. 190, Oct. 24, 1975; pp. 377–379.

Blakemore, R. P., Maratea, D. & Wolfe, R. S., *Journal of Bacteriology,* Nov. 1979, vol. 140, No. 2; pp. 720–729.

Frankel, R. B., Blakemore, R. P. & Wolfe, R. S., *Science,* Mar. 30, 1979, vol. 203, pp. 1355–1356.

*Primary Examiner*—Raymond N. Jones
*Assistant Examiner*—Elizabeth J. Curtin
*Attorney, Agent, or Firm*—Cooper, Dunham, Clark, Griffin & Moran

[57] ABSTRACT

A biologically pure culture of a bacterium of the genus Aquaspirillum, designated MS-1, has been found to contain chains (so-called magnetosomes) of single domain magnetite particles. The magnetite particles are roughly cubic and are about 500 Å on a side. Each of the chains contains approximately 20 magnetite particles. These magnetite particles can be recovered from the bacterium and usefully employed in magnetic recording devices and the like. The biologically pure culture of the magnetic bacterium may be grown in a low oxygen environment and on a nutrient medium containing ferric quinate.

27 Claims, 4 Drawing Figures

CULTURE MEDIUM AND CONDITIONS FOR GROWTH OF MAGNETIC BACTERIA

BACKGROUND OF THE INVENTION

The invention described herein was made in the course of a grant from the National Science Foundation.

This application is related to an application filed Mar. 27, 1980 by one of the inventors herein (Blakemore) entitled "Magnetic Bacteria And Products Derived Therefrom."

This invention relates to a biologically pure culture of magnetic bacteria and to a culture medium and conditions for growing the biologically pure culture of magnetic bacteria.

Magnetic bacteria were first reported by Blakemore in *Science*, 190, 377 (1975). Several species of these bacteria, extracted from both fresh water and marine environments, were observed to orient and to swim in a preferred direction relative to the geomagnetic field. Magnetic bacteria from the Northern Hemisphere were observed to orient and swim towards the North, while it was predicted (and later confirmed) that magnetic bacteria from the Southern Hemisphere would orient and swim towards the South. Reversal of the ambient magnetic field, e.g., by Helmholz coils, caused the cells to reverse directions within one second. Killed cells also oriented in uniform fields as low as 0.1 G. In this and other respects, the cells behaved like single magnetic domains in a ferromagnetic material.

The magnetotactic behavior of the bacteria was attributed to cellular iron localized in crystal-like particles, 1000 to 1500 Å long within the bacteria. As reported above, the bacteria contained these iron-rich particles arranged in chains. Each cell had one or two of these chains, consisting of five to ten particles apiece. Clumps of the particles were also observed outside of the cells. It was speculated that the iron-containing particles equip the bacteria with a permanent ferromagnetic dipole moment.

SUMMARY OF THE INVENTION

Definitive studies of the chemical nature of the iron in magnetotactic bacteria has not been possible up to now because the organisms have not been available in pure culture. By means of the present invention, a biologically pure culture of magnetic bacteria may be cultured under specific conditions on a special growth medium rich in iron.

The special growth or culture medium of the present invention is an aqueous solution comprising, per 100 ml, about 2-30 $\mu$M of ferric quinate, about 10-1000 mg of an organic compound selected from the group consisting of fumaric acid, tartaric acid, malic acid, succinic acid, lactic acid, pyruvic acid, oxaloacetic acid, malonic acid, $\beta$-hydroxybutyric acid, maleic acid, galactose, rhamnose, melibiose, acetic acid, adipic acid, and glutaric acid, a vitamin source, a mineral source, a nitrogen source, an acetate source, and pH buffer.

In a preferred embodiment, the culture medium comprises, per 100 ml, about 2-30 $\mu$M of ferric quinate, about 10-1000 mg of an organic acid selected from the group consisting of fumaric, tartaric, malic, succinic, lactic, pyruvic, oxaloacetic, malonic, $\beta$-hydroxybutyric, and maleic acid, about 0.25-2 ml of a vitamin elixir, about 0.25-2 ml of a mineral elixir, about 1-100 mg of an ammonium or nitrate source, such as ammonium chloride or sodium nitrate, about 2-100 mg of acetic acid or a salt of acetic acid, such as sodium acetate, about 0.1-5 mM of a phosphate buffer, such as potassium dihydrogen phosphate, and about 2.5-50 mg of a reducing agent, such as sodium thioglycolate.

A biologically pure culture of magnetic bacteria, such as a new strain of bacteria designated MS-1, may be grown by preparing the above-described culture medium, adjusting the pH of the culture medium within the range of about 5.2-7.5, sterilizing, for example by boiling or autoclaving, the culture medium, inoculating the culture medium with magnetic bacteria, providing the bacteria with an initial oxygen concentration in the range of about 0.2-6% by volume, and maintaining the ambient temperature in the range of about 18°-35° C.

The culture medium of the present invention has been used to grow a biologically pure culture of a new strain of bacteria designated MS-1. MS-1 is a magnetotactic Aquaspirillum. A non-magnetic variant of the stain may be cultured from MS-1 with a growth medium lacking iron or when the bacteria are provided with abundant $O_2$ (more than 6% by volume). The iron-rich particles in MS-1 were found to be comprised of the mineral magetite, $Fe_3O_4$. Frankel, Blakemore, and Wolfe, *Science*, 203, 1355 (1979).

Magnetite may be extracted from the magnetotactic cells in the form of a coated chain of single domain particles. These particles are roughly cubic, about 500 Å on a side. Each chain contains about 20 particles. The chain of magnetite particles together with their bonding layers or envelopes have been termed "magnetosomes." The magnetosomes are unusual structures which find many useful applications, such as on magnetic recording tape.

DETAILED DESCRIPTION OF AN EMBODIMENT OF THE INVENTION

Figure 1:
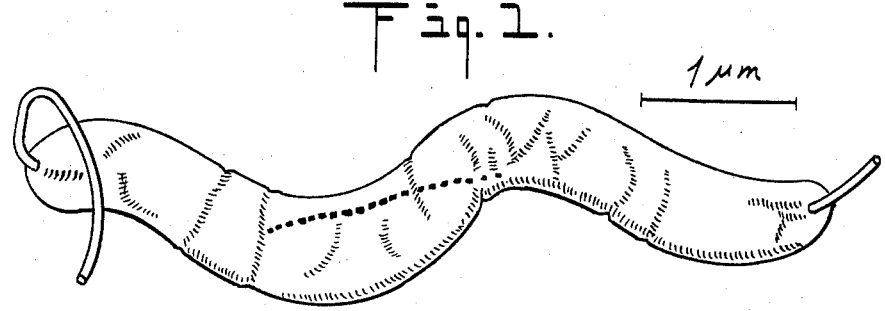
FIG. 1 is an illustration of an isolated cell of strain MS-1 showing the magnetite particles.

A magnetotactic bacterium was isolated from fresh water swamps and was cultured in the laboratory on the special growth medium of the present invention. Frankel, Blakemore, and Wolfe, *Science*, 203, 1355 (1979). The organism is a magnetotactic Aquaspirillum and appears to be a new bacterial species by criteria separate from its magnetic properties. It has been designated strain MS-1. A culture of this microorganism has been deposited in the permanent collection of the American Type Culture Collection, Rockville, Md. A subculture of the microorganism may be obtained upon request. Its accession number in this repository is ATCC 31632.

Isolation and Growth of Strain MS-1

Inocula for isolating magnetic bacteria were initially obtained from enriched bog water by application of magnetic fields. Blakemore, Maratea, and Wolfe, *J. Bact.*, 140, 720 (1979). Permanent bar magnets were used to separate large numbers of motile magnetic cells from sediment. These magnetotactic cells (of at least six distinct morphological types) were washed in filtered, sterilized bog water and injected through the stoppers of culture tubes containing a prereduced, semisolid isolation medium. The isolation medium consisted of (per 90 ml of distilled water): 10 ml of filtered swamp or bog water; 1 ml of vitamin elixir and 1 ml of mineral elixir [Wolin, Wolin, and Wolfe, *J. Biol. Chem.*, 238, 2882 (1963)]; and 0.5 mM potassium dihydrogen phosphate buffer (pH 6.7). To this mixture were added: 5 µg of vitamin B-12, 25 mg of ammonium chloride ($NH_4Cl$); 10 mg of sodium acetate (anhydrous); 0.2 mg of resazurin; and 90 mg of Ionagar No. 2 (Oxoid). The pH was adjusted to 6.7 with NaOH. This isolation medium was prereduced under nitrogen, using titanium citrate as the reducing agent, and was subsequently dispensed into culture tubes in an anaerobic hood. Inoculated tubes were incubated at 22° C. in the dark until growth became evident. A well-isolated area of growth was homogenized, and cells were cloned by serial dilution into tubes containing molten, prereduced isolation medium containing 0.85% (wt/vol) Ionagar No. 2. Well-isolated colonies which appeared in these tubes after one week at 30° C. were homogeneous as evidenced by microcopy. However, cells were again cloned, and the process was repeated a third time before cultures were considered pure.

Strain MS-1 was maintained at 30° C. with weekly transfers in screw-capped culture tubes containing a semisolid growth or culture medium consisting of (per 98 ml of distilled water): 1 ml of vitamin elixir; 1 ml of mineral elixir; 5 mM of potassium dihydrogen phosphate ($KH_2PO_4$); 25 µM ferric quinate; and 0.2 mg of resazurin. To this mixture were added (per 100 ml): 0.1 g of succinic acid; 20 mg of sodium acetate (anhydrous); 10 mg of sodium nitrate ($NaNO_3$); 5 mg of sodium thioglycolate; and 130 mg of agar (GIBCO Laboratories). The ferric quinate solution was prepared by combining 2.7 g of $FeCl_3$ and 1.9 g of quinic acid with 1 liter of distilled water. Before adding the agar, the pH of the medium was adjusted to 6.7 with NaOH. The medium was boiled, and 12 ml was added to each screw-capped tube (16 by 125 mm) containing approximately 0.1 ml of 5% (wt/vol) sodium thioglycolate in distilled water. Tubes of semisolid growth medium were autoclaved with caps tightened and allowed to stand overnight for the establishment of $O_2$ gradients. Inocula consisted of 0.2 ml (ca. $7 \times 10^7$) cells per 12 ml of medium. A chemically defined growth medium was identical to the semisolid growth medium, except that agar was omitted and the medium was sealed under a gas atmosphere of known composition as described below.

A homogeneous population of nonmagnetic cells was obtained from cultures of MS-1 grown in the isolation medium made with distilled water rather than bog water. Cells grown in the medium, especially with twice as much as the usual amount of nitrate and succinate, grew nonmagnetically. To obtain a nonmagnetic culture from the strain MS-1 for comparative studies, cells grown for five successive transfers in this medium were cloned three successive times. Stocks of this nonmagnetic variant of strain MS-1 were subsequently maintained in the chemically defined growth medium without ferric quinate.

Cells of strain MS-1 in the magnetic and nonmagnetic state were mass cultured in the chemically defined growth medium and in this medium minus ferric quinate, respectively. Agar was omitted from media for mass cultures. Glass bottles (150 ml to 1 liter) were filled to approximately one-third of their volume with medium. The atmosphere of each was replaced with $N_2$, and it was then crimp-sealed with a serum stopper or closed with a rubber stopper wired in placed before autoclaving. Cells were inoculated into cooled medium by injection through the stopper. Sufficient air was added to each bottle at the time of inoculation to provide 0.6 to 1.0% (vol/vol) $O_2$ in the gas phase for routine culture. Growth of magnetic cells was inhibited when the initial $O_2$ concentration was above about 6%. However, nonmagnetic cells grew at these higher $O_2$ concentrations.

A glass carboy was sealed with a rubber stopper fitted with a bottomless, screw-capped, 16-mm tube which served as a gas outlet and port for inoculation and sampling. A 12-g stainless needle which had been inserted through the stopper was used as a gas inlet. It was attached to a 40-cm length of tubing contained within the carboy to allow incurrent gas to sparge through the culture medium. The medium in each carboy was autoclaved under air. Hot medium was sparged with sterile $N_2$ while being cooled at 30° C. It was then inoculated and incubated at 30° C. after sealing the carboy against further gas exchange. Midway through growth, when the culture became reduced as evidenced by a color change, its pH was adjusted to 6.7 aseptically with 0.5 M succinic acid, and it was continuously aerated with sterile air by means of an aquarium pump.

A variety of organic compounds in addition to succinic acid can be used as carbon and energy sources in the growth medium. Those which support growth of MS-1 are intermediates of the tricarboxylic acid cycle, such as fumaric, malic, succinic, oxaloacetic, malonic, and maleic, as well as β-hydroxybutyric, tartaric, lactic, and pyruvic acids. Other organic compounds which support weak growth include, galactose, rhamnose, melibiose, acetic acid, adipic acid, and glutaric acid.

Nitrogen or nitrates are desirable ingredients of the growth medium. When nitrogen is not provided in the growth medium, the bacteria apparently utilize nitrogen from the atmosphere. However, in such case, growth yield of the cells is poor. In some cases, the cells did not grow without the nitrate, and in other cases, cell growth was markedly improved with the addition of $NaNO_3$ or $NH_4Cl$.

Phosphate is another desirable ingredient of the culture medium. In the embodiment described above, $KH_2PO_4$ serves as both a pH buffer and as a source of phosphate.

Resazurin is a redox indicator. It is used in the embodiment described above to indicate whether the bacteria are growing aerobically or anaerobically. It may be omitted from the culture mediu. Sodium thioglycolate functions as a reducing agent. It too may be omitted from the culture medium provided the bacteria are grown in an atmosphere low in oxygen.

Ferric quniate is not required for cell growth but without it, the cells are not magnetotactic. Neither ferric chloride, ferric citrate, nor iron chelated by L-DOPA, protocatechuic acid, L-epinephrine, L-arterenol, or EDTA satisfied the requirement for $Fe_3O_4$ synthesis by MS-1.

Vitamins are not required for growth or magnetotactic behavior of the organism but do prevent the cells from acquiring a swollen appearance. The vitamin elixir used in the above-described embodiment contained the following vitamins per liter of water: biotin, 2 mg; folic acid, 2 mg; B$_6$ (pyridoxine) hydrochloride, 10 mg; B$_1$ (thiamine) hydrochloride, 5 mg; B$_2$ (riboflavin), 5 mg; nicotinic acid (niacin), 5 mg; pantothenic acid (DL-calcium pantothenate), 5 mg; B$_{12}$ crystalline (cyanocobalamin), 100 μg, PABA (para-aminobenzoic acid), 5 mg; and lipoic acid, 5 mg.

The mineral elixir used in the above-described embodiment contained the following minerals per liter of water: nitrilotriacetic acid, 1.5 g; MgSO$_4$.7H$_2$O, 3.0 g; MnSO$_4$.H$_2$O, 0.5 g; NaCl, 1.0 g; FeSO$_4$.7H$_2$O, 0.1 g; CoSO$_4$ or CoCl$_2$, 0.1 g; CaCl$_2$, 0.1 g; ZnSO$_4$, 0.1 g; CuSO$_4$.5H$_2$O, 0.1 g; AlK(SO$_4$)$_2$, 0.01 g; H$_2$CO$_3$, 0.01 g; and NaMoO$_4$ (sodium molybdate), 0.01 g.

Structure of Magnetic Bacteria and Isolated Magnetic Components

Magnetotactic cells of strain MS-1 possess a right-handed helical morphology. Each cell has single bipolar flagella (FIG. 1). The cell envelope of strain MS-1 appears in thin sections to consist of two distinct layers, a lipopolysaccharide (LPS) or "wall membrane" and a cytoplasmic membrane. The wall member is trilaminate in cross-section. Two types of inclusion bodies are present within the cytoplasm, (i) those with a structure resembling poly-β-hydroxybutyrate (PHB) granules and (ii) iron-rich particles, described in detail below.

Magnetotactic cells of strain MS-1 contain 2.0±0.2% (wt/vol) of their dry weight in iron. Nonmagnetotactic cells of strain MS-1 lack the iron-rich particles of the magnetic cells. Magnetic cells contain 10 times more iron than non-magnetic cells on a dry weight basis. However, the disparity is even greater than the dry weight figures because of the large weight contribution of iron. In all respects aside from the magnetic properties and the presence of the iron particles, the magnetic and nonmagnetic cells of strain MS-1 are similar.

Electron microscopy confirms that magnetotactic cells and coccoid bodies of spirillum strain MS-1 contains intracellular chains of electron-dense, iron-rich particles similar to those observed previously in other magnetotactic bacteria. These particle chains, which are not known to occur in other spirilla, do not resemble any of the various known types of inclusion bodies in nonmagnetotactic bacterial cells. They are novel bacterial cell components, the ultrastructure of which has not yet been thoroughly studied.

Figure 3:
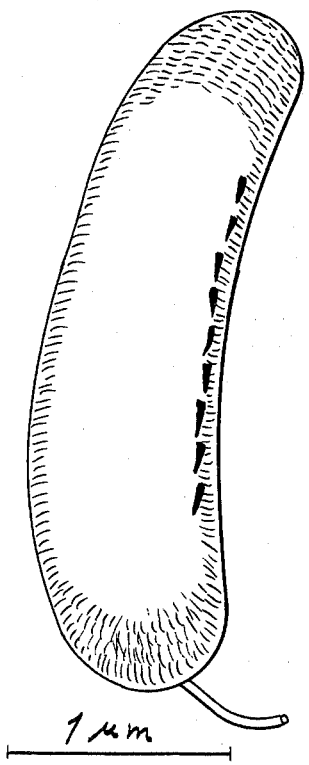
FIG. 3 is an illustration of a magnetic bacterium having pyromidal-shaped magnetic particles.
Figure 2:
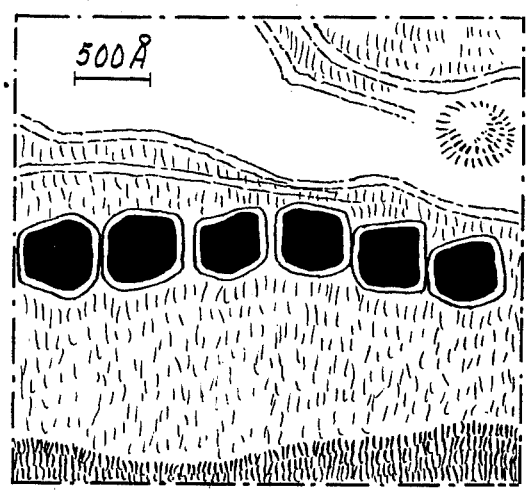
FIG. 2 is an illustration of the magnetite particles of MS-1 under higher magnification.
Figure 4:
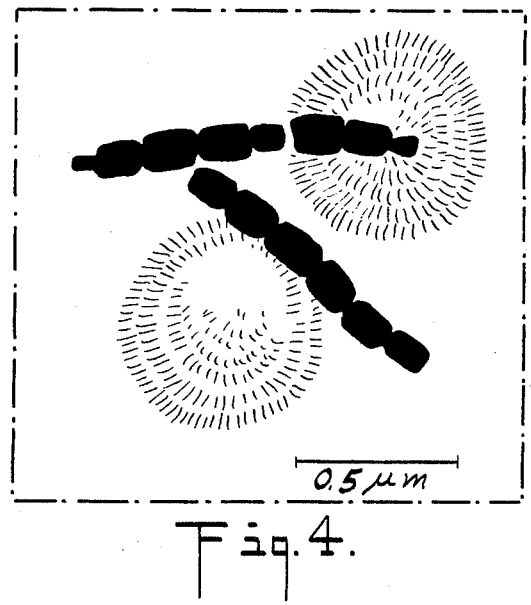
FIG. 4 is an illustration of parallelpipied-shaped magnetic particles in a magnetic bacterium.

High resolution scanning electron microscopy of the iron-rich particles shows that most of them are roughly cubic with rounded corners, although some of them may be described as octahedral. Thus, the particles are similar to those found in other magnetotactic bacteria (FIG. 4), with the exception of some varieties found in the Southern Hemisphere, which have iron-rich particles of pyramidal or arrowhead shape (FIG. 3).

The size of the particles in MS-1 varied from 250 to 550 Å in width, the average length of a side being about 420 to 500 Å. Energy dispersive X-ray measurements show that the particles in strain MS-1 have high iron content. Mossbauer spectroscopy of $^{57}$Fe conclusively shows that the iron in the particles is magnetite, Fe$_3$O$_4$, with possibly minor admixture of γ-Fe$_2$O$_3$ and another iron-containing compound similar to ferritin. *Science,* 203, 1355 (1979). Non-magnetotactic cells lack the magnetite crystals. Thus, magnetotaxis in MS-1 is associated with intracellular magnetite. The presence of intracellular magnetite is evidence of a process of bacterial synthesis from the soluble (chelated) iron contained in the growth medium.

When viewed in negatively-stained preparations of whole cells, the electron-dense particles are arranged in a single chain that runs the length of the cell in a generally straight line. The number of particles in each chain varies from about 5 to about 50, averaging about 20 particles per chain. The largest particles are located in the center of the chain, while those at the ends are often smaller. While magnetic forces may help to hold the particles together in chains, it seems likely that they are also connected structurally. This has been confirmed by electron microscopy which shows that the particles are enveloped by membranes.

When viewed in thin-sectioned preparations, each particle is surrounded by an inner electron-transparent layer 16 Å thick and by an outer electron-dense layer 14 Å thick. Adjacent particles in a chain are sometimes in direct contact with each other, but usually are separated by a distance of 30–190 Å. The space between the particles does not appear to contain distinct structures though cytoplasmic material appears to be present there.

The layers surrounding the particles are still uncharacterized. The electron-dense layer could be a protein "membrane" similar to those observed surrounding other types of bacterial inclusion bodies. However, the protein "membrane" of other inclusion bodies is not separated from the body by an electron-light layer. It is possible that the electron-dense layer is a true biological membrane (e.g., a lipid bilayer) rather than a protein structure. It is also conceivable that the membrane is actually trilaminate but that the inner-most layer, being electron-dense, cannot be distributed from the particle itself. Additional studies are needed to ascertain the true chemical nature of the layers.

The chains appear to be a stable structural characteristic of the particles. The particles remain arrayed in chains in degenerate cell forms termed coccoid bodies which develop under adverse conditions. The chains may be extracted from the cells of MS-1 by a variety of methods. For example, they may be extracted by mechanical means, such as sonication, or by chemical disruption or lysis of the cells with sodium dodecyl sulfate. The chains may then be purified by treatment with sodium dodecyl sulfate and then collected by centrifugation or with a magnet after being extracted from the cells.

In view of their unique structure and chemical nature, as well as their role in bacterial magnetotaxis, the chains of particles together with their bounding layers have been termed "magnetosomes." The magnetosomes exhibit magnetic remanence, orient in externally applied magnetic fields, and have an X-ray diffraction spectrum characteristic of magnetite. Since they, or structures similar to them, have been reported in all magnetotactic bacteria described to date, but have not been observed in any non-magnetotactic cells, there can be little doubt that they are directly responsible for the alignment of magnetic cells in magnetic fields. This is also supported by theoretical calculations.

The magnetic properties of magnetite particles depend on their size and shape. For a particle of roughly cubic shape with side dimension d, there is a range of d over which the particle will be a single magnetic domain. Butler and Banerjee, *J. Geophys. Res.,* 80, 4049, (1973), calculated that at 300° K., magnetite particles will be single domain if d is within the range of 500 to 700 Å. Thus, with d=500 Å, the magnetite particles in strain MS-1 are within the single domain size range.

The magnetic properties of a chain of single domain particles have been considered by Jacobs and Bean, *Phys. Rev.*, 100, 1060 (1955). Their results showed that because of strong interparticle interactions, the preferred orientation of the individual particles is such that their axes of magnetization are parallel, north-to-south along the chain direction. Thus, the entire chain acts as a single magnetic dipole with a moment equal to the sum of the particle moments. They also calculated the applied field necessary to cause reversal of the chain magnetization, postulating a fanning mechanism for individual moment reversal. This mechanism requires an applied field of several hundred gauss to induce reversal in a chain of magnetite particles, in qualitative agreement with experimental results obtained using magnetic bacteria. Kalmijn and Blakemore in *Animal Migration, Navigation and Homing*, K. Schmidt-Koenig and W. T. Keeton, Eds. (Springer Verlag, N.Y., 1978), p. 344.

The magnetic moment per bacterium, M, can be calculated using the known magnetic moment per unit volume of magnetite, $M_v = 480$ emu/cc. For a single particle of volume $1.25 \times 10^{-16}$ cc, the magnetic moment $m = 6.1 \times 10^{-14}$ emu. For a cell containing an average chain length of 22 particles, the total moment per bacterium $M = 1.3 \times 10^{-12}$ emu. In the geomagnetic field of 0.5 G, the total magnetic energy of a cell $MH = 6.6 \times 10^{-13}$ erg. This value is over an order of magnitude greater than the thermal energy, $kT$ ($4.1 \times 10^{-14}$ erg at 300° K.).

The orientation of a bacterium or equivalently, the orientation of an ensemble of bacteria in the earth's magnetic field of 0.5 G in water at ambient temperatures can be calculated from the well-known Langevin theory of classical paramagnetism. The calculations show that each bacterium contains a sufficient but not an excessive amount of single domain sized magnetite in an appropriate configuration to produce orientation in the earth's magnetic field at ambient temperature, i.e., the cell's chain of magnetite crystals functions as a biomagnetic compass.

The simplest hypothesis for the mechanism of magnetotaxis is passive orientation of the bacterium resulting from the torque exerted by the ambient magnetic field on its biomagnetic compass as it swims. An estimate of the rotation time for a bacterium in water can be obtained from the rotational diffusion equation. Calculations of this nature show that the time required to reorient 180° in response to a sign reversal of a 0.5 G magnetic field is about 0.4 sec. This result is of the order of reversal times measured by Kalmijn and Blakemore for bacteria taken from mud samples.

Since most magnetotactic bacteria from the Northern Hemisphere are observed to swim northward and hence downward, the compass in these cells must have a fixed orientation with respect to the flagellum, with the north seeking pole opposite the flagellum. Analogously, bacteria from the Southern Hemisphere have the south seeking pole opposite the flagellum. Blakemore, Frankel, and Kalmijn, *Nature*, 286, 384 (1980). This orientation could be preserved in cell division if the compass is partitioned between two daughter cells. Subsequently, during the magnetite biosynthesis, the magnetic moments of nascent magnetite particles at the ends of the pre-existing chains would become oriented along the chain direction by interaction with the chain dipole moment.

Both strain MS-1 and its inclusion bodies may have useful applications. For example, the magnetosomes or the single domain magnetite crystals may find use in connection with magnetic recording tape or in connection with medical applications. Other uses will undoubtedly be found for both the bacterium and its inclusion bodies.

While the invention has been described by reference to specific examples, these references are for purposes of illustration only, and should not be construed to limit the spirit or scope of the invention.

We claim:

1. An aqueous culture medium for the growth of a biologically pure culture of magnetic bacteria, comprising, per 100 ml, about 2–30 μM of ferric quinate, about 10–1000 mg of an organic compound selected from the group consisting of fumaric acid, tartaric acid, malic acid, succinic acid, lactic acid, pyruvic acid, oxaloacetic acid, malonic acid, β-hydroxybutyric acid, maleic acid, galactose, rhamnose, melibiose, acetic acid, adipic acid, and glutaric acid, a vitamin source, a mineral source, a nitrogen source, an acetate source, and a pH buffer, said pH buffer resulting in a pH of said aqueous culture medium of about 5.2–7.5.

2. An aqueous culture medium in accordance with claim 1 wherein said vitamin source comprises about 0.25–2 ml of a vitamin elixir.

3. An aqueous culture medium in accordance with claim 1 wherein said mineral source comprises about 0.25–2 ml of a mineral elixir.

4. An aqueous culture medium in accordance with claim 1 wherein said nitrogen source comprises about 1–100 mg of an ammonium ion or nitrate ion source.

5. An aqueous culture medium in accordance with claim 1 wherein said acetate source comprises about 2–100 mg of acetic acid or a salt of acetic acid.

6. An aqueous culture medium in accordance with claim 1 wherein said pH buffer comprises about 0.1–5 mM of a phosphate buffer.

7. An aqueous culture medium in accordance with claim 1 also containing a reducing agent.

8. An aqueous culture medium in accordance with claim 7 wherein said reducing agent comprises about 2.5–50 mg of sodium thioglycolate.

9. An aqueous culture medium for the growth of a biologically pure culture of magnetic bacteria, comprising, per 100 ml, about 2–30 μM of ferric quinate, about 10–1000 mg of an organic acid selected from the group consisting of fumaric acid, tartaric acid, malic acid, succinic acid, lactic acid, pyruvic acid, oxaloacetic acid, malonic acid, β-hydroxybutyric acid, and maleic acid, a vitamin source, a mineral source, about 1–100 mg of an ammonium ion or nitrate ion source, about 2–100 mg of acetic acid or a salt of acetic acid, about 0.1–5 mM of a phosphate buffer, about 2.5–50 mg of sodium thioglycolate, and the remainder substantially distilled water.

10. An aqueous culture medium in accordance with claim 9 wherein said organic acid is succinic acid.

11. An aqueous culture medium in accordance with claim 9 wherein said vitamin source comprises about 0.25–2 ml of a vitamin elixir.

12. An aqueous culture medium in accordance with claim 9 wherein said mineral source comprises about 0.25–2 ml of a mineral elixir.

13. An aqueous culture medium in accordance with claim 9 wherein said ammonium ion source is ammonium chloride.

14. An aqueous culture medium in accordance with claim 9 wherein said nitrate ion source is sodium nitrate.

15. An aqueous culture medium in accordance with claim 9 wherein said salt of acetic acid is sodium acetate.

16. An aqueous culture medium in accordance with claim 9 wherein said phosphate buffer is potassium dihydrogen phosphate.

17. An aqueous culture medium for the growth of a biologically pure culture of magnetic bacteria, comprising, per 100 ml, about 25 μM ferric quinate, about 100 mg of an organic acid selected from the group consisting of fumaric acid, tartaric acid, malic acid, succinic acid, lactic acid, pyruvic acid, oxaloacetic acid, malonic acid, β-hydroxybutyric acid, and maleic acid, a vitamin source, a mineral source, about 10 mg of a nitrate source, about 20 mg of acetic acid or a salt of acetic acid, about 5 mM of a phosphate buffer, about 5 mg of sodium thioglycolate, and the remainder substantially distilled water.

18. An aqueous culture medium in accordance with claim 17 wherein said organic acid is succinic acid.

19. An aqueous culture medium in accordance with claim 17 wherein said vitamin source comprises about 1 ml of a vitamin elixir.

20. An aqueous culture medium in accordance with claim 17 wherein said mineral source comprises about 1 ml of a mineral elixir.

21. An aqueous culture medium in accordance with claim 17 wherein said nitrate source is sodium nitrate.

22. An aqueous culture medium in accordance with claim 17 wherein said salt of acetic acid is sodium acetate.

23. An aqueous culture medium in accordance with claim 17 wherein said phosphate buffer is potassium dihydrogen phosphate.

24. An aqueous culture medium in accordance with claim 1, 12, or 20 also containing agar.

25. A method for preparing a culture medium for the growth of a biologically pure culture of magnetic bacteria, comprising mixing together the ingredients of claim 1, 9, or 17, adjusting the pH of the mixture within the range of about 5.2–7.5, and sterilizing the mixture.

26. A method for preparing a culture medium in accordance with claim 25 wherein the pH is adjusted to about 6.7.

27. A method for preparing a culture medium in accordance with claim 25 wherein the mixture is sterilized by boiling or autoclaving.

* * * * *